(12) United States Patent
Talamini

(10) Patent No.: US 8,449,550 B2
(45) Date of Patent: May 28, 2013

(54) IP PRECISION BLADE GUIDE

(75) Inventor: Victor J. Talamini, Asbury Park, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 274 days.

(21) Appl. No.: 12/943,306

(22) Filed: Nov. 10, 2010

(65) Prior Publication Data

US 2012/0116406 A1    May 10, 2012

(51) Int. Cl.
*A61F 5/00* (2006.01)

(52) U.S. Cl.
USPC .................................. 606/87; 606/79; 606/82

(58) Field of Classification Search
USPC .................. 606/79, 82–85, 86 R, 87
See application file for complete search history.

(56) References Cited

U.S. PATENT DOCUMENTS

| | | | |
|---|---|---|---|
| 5,100,407 A | 3/1992 | Conrad et al. | |
| 5,147,364 A | 9/1992 | Comparetto | |
| 5,725,530 A | 3/1998 | Popken | |
| 5,908,423 A | 6/1999 | Kashuba et al. | |
| 6,395,004 B1 | 5/2002 | Dye et al. | |
| 2006/0009796 A1 | 1/2006 | Carusillo et al. | |
| 2007/0119055 A1 | 5/2007 | Walen et al. | |
| 2007/0233243 A1 | 10/2007 | Sudmann | |

OTHER PUBLICATIONS

Stryker Precision Oscillating Tip Saw, Stryker 2006.

*Primary Examiner* — Andrew Yang
(74) *Attorney, Agent, or Firm* — Lerner, David, Littenberg, Krumholz & Mentlik, LLP

(57) ABSTRACT

A bone resection system for a prosthetic implant having an anterior and posterior outer surface attached to bone has a cutting guide having slotted guide surfaces thereon mountable on the prosthetic implant. The guide surfaces are alignable with the implant outer anterior and posterior surfaces. A saw comprising a housing having spaced apart first and second sides joined by first and second edge surfaces and having a proximal end and a distal end can be inserted into the slotted guide surfaces. A cutting head drive system on the housing drives a cutting head having teeth extending outwardly of the distal end of the housing. A cam element is mounted on the saw housing intermediate the proximal and the distal ends. The cam element has a distal end with a guide arm extending therefrom engagable, during insertion, with the guide surface on the cutting guide. The cam element having a stop surface for engaging a stop surface on the cutting guide to limit blade travel.

14 Claims, 12 Drawing Sheets

IP PRECISION BLADE GUIDE

BACKGROUND OF THE INVENTION

Total hip arthroplasty and total arthroplasty have become increasingly useful methods of treating hip and knee joint disease. While great progress has been made in extending the life of prosthetic orthopedic implants, it is still necessary, in some cases, to perform revision surgeries which require the removal of already implanted hip and knee joint prosthetic components. Each prosthetic removal should avoid damage to the surrounding soft tissue and bone while conserving as much bone as possible. Current procedures do not control damage precisely.

Such removal of prosthetic implants requires the loosening of the implants which are fixed in the femur either by bone cement or ingrown tissue which fills porous surfaces on an implant designed for non-cemented attachment. A hammer and chisel are typically used to split the bone to loosen the implant causing trauma to the femur and complicating the procedure in both interval and complexity. The osteotome is another typically used tool to sever the interconnection between the typically metallic prosthesis and surrounding tissue or bone cement. Such a procedure is time consuming and tedious and runs the risk of damaging the femur when removing a femoral component from the intramedullary canal of a femur.

Recently there has been proposed a new procedure for removing a femoral prosthesis that removes a minimum of bone. A Stryker® Precision™ Oscillating Tip Saw is a surgical tool that is powered by a hand piece that houses a motor and the complimentary controlled circuit that regulates the actuation of the motor. This saw has a static planar guide bar that extends forward (distally) from the hand piece and has a planar saw blade. Typically the most forward or distal end of the saw blade is formed with teeth for cutting hard tissue against which the blade is applied. A drive mechanism internal to the handpiece transfers the power developed by the motor to the blade. More particularly, the drive mechanism converts the rotary motion produced by the output shaft of the handpiece moves the blade in an oscillatory, back-and-forth pattern in the plane in which the blade is aligned. Consequently, when the Precision™ saw is actuated, the blade teeth move in back-and-forth pattern against the hard tissue or bone to which the teeth are applied. As a consequence of this motion and the forward pressure applied by the surgeon holding the saw, the teeth cut and separate the hard tissue or bone from the implant tissue ingrowth surfaces.

In order to ensure that the proper cut lines are formed in the bone, the surgeon typically first mounts a cutting guide, sometimes called a jig, to the bone adjacent to the location where the cut is to be made. One type of cutting guide is in the form of a block formed with a precisely shaped set of slots. The slots define the lines along which the bone is to be cut. The surgeon then performs a surgical procedure by sequentially inserting the saw blade in the slots. Once the blade is inserted in a slot, the saw is actuated. In this manner, the surgeon is able to cut the bone or hard tissue along the precisely defined lines along which the bone is to be separated.

A saw of this type is disclosed in U.S. Patent Publication No. 2006/0009796 the disclosure of which is incorporated herein by reference. The saw disclosed therein is used by actuating a motor internal to the hand piece. The drive assembly transfers the power developed by the motor to the drive rod so that the rod simultaneously engage in a back-and-forth reciprocating motion in opposite directions. The drive rods, in turn, transfer the reciprocating motion to the saw blades so that the blade teeth move in a back-and-forth or side-to-side oscillating motion.

BRIEF SUMMARY OF THE INVENTION

The removal of an osteointegrated implant, for example a proximal portion of a femoral component previously implanted in the proximal femur, requires the precise cutting of the integrated tissue along the anterior and posterior sides of the proximal portion of the femoral implant. Use of a Precision™ sagittal saw with its oscillating motion, guide block and cam makes it possible for precise resections along the anterior and posterior sides of the implant without violating medial or lateral boundaries of the implant. The distal motion is limited by the cam thereby removing only the tissue bordering the anterior, distal and posterior surfaces of the implant thereby conserving tissue guided by precisely positioned slots in the guide, static planar guide housing and cam guide block fixedly attached to the proximal femoral component can be utilized. Such a guide block can be fixedly attached adjacent the neck of the femoral component. The guide slots aligned with the interface between the anterior and posterior faces of the femoral component where it integrates into adjacent tissue. End walls of the guide slot in contact with the cams can be used to precisely direct the oscillating distal end of the saw for cutting the precise medial-lateral dimensions of the anterior and posterior femoral component surfaces.

A bone resection system of this type is used with a prosthetic implant having an anterior and posterior outer surface attached to bone. A cutting guide is provided having a saw guide surface or surfaces thereon mountable on the prosthetic implant preferably in the neck area. The guide slot surfaces extend in a medial-lateral and proximal-distal direction and are alignable with the implant anterior and posterior outer surfaces. A saw is provided comprising a housing having spaced apart first and second sides joined by first and second edge surfaces and having a proximal end and a distal end. A cutting head drive system on the housing drive a cutting head having teeth extending outwardly of the distal end of the housing. At least one cam element is mounted on the saw housing intermediate the proximal and the distal ends of the blade. The cam element has a distal end with a guide arm extending therefrom engagable with the medial and/or lateral guide surfaces on the cutting guide. The cam element has a stop surface for engaging a stop surface on the cutting guide. The guide surface on the cutting guide has opposed first and second end surfaces extending generally perpendicular to the implant outer surface. The first and second end surfaces are oriented at an angle to one another respectively for engaging the first and second sides of the housing.

The prosthetic implant is a prosthetic femoral component having a neck portion coupled to a distally extending stem portion and the cutting guide is mountable adjacent the neck portion. The saw guide slotted surfaces of the cutting guide are aligned with both the anterior-posterior and the medial and lateral sides of the femoral component. The medial and lateral guide surfaces are aligned so that the entire anterior-posterior extent of the ingrowth surfaces can be cut. The cutting guide includes a passageway for receiving the neck portion of the femoral component and a posterior surface for coupling the cutting guide to the femoral component. The cutting guide has an anterior opening and a posterior opening respectively aligned with the anterior and posterior outer surfaces of the femoral component. A cam element has an opening for receiving the saw. The cutting guide medial and lateral openings are rectangular openings for receiving an outer surface of the saw housing and the cam element. The rectangular opening in the cam element is formed when in use, by medial and lateral end walls and longer anterior and posterior sidewalls, the two end walls contacting the first and second sides of the saw housing. The guide arm of the cam element extends from one end wall but is not limited to one end wall. The guide arm has a leading surface with an outer surface tapered towards the housing and forming a tip adjacent the housing.

The system may include an attachment element extending between the cam element and the housing for locking the cam element on the housing. The two longer sidewalls of the rectangular opening slidably receive the housing first and second sides. The distance between the end walls of the rectangular guide opening is greater than a distance between the edges of the housing. The cam element opening is appropriately to receive the Precision™ saw blade and cam. The cam arm fits within this slot while the distal surface of the cam element acts as a stop when it contacts the guide proximal surfaces. The cutting guide includes a threaded fastener for coupling the cutting guide to the prosthetic implant.

DETAILED DESCRIPTION

Figure 1:
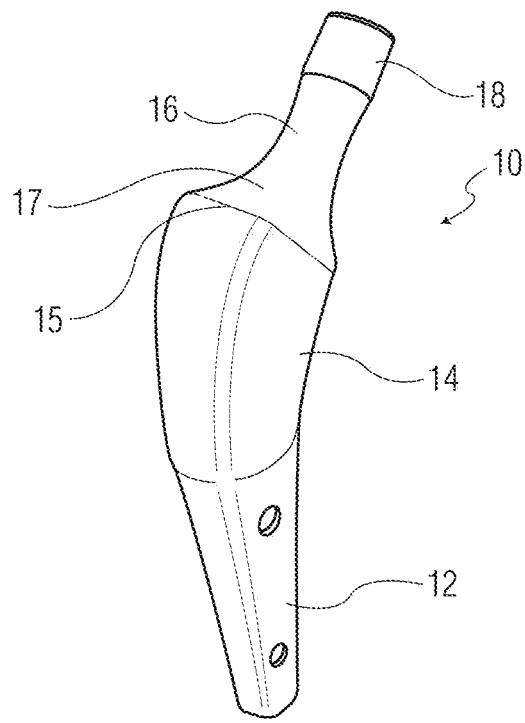
FIG. 1 is a perspective view of a typical femoral component having a proximal tissue ingrowth area on the anterior, posterior, medial and lateral sides.
Figure 1A:
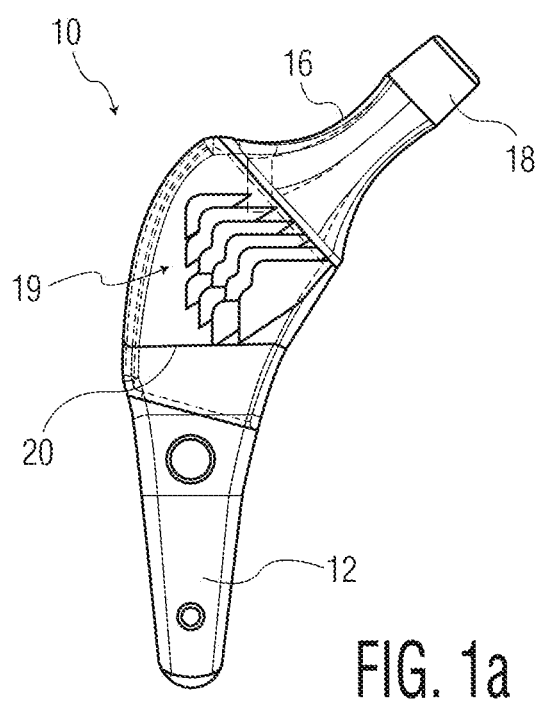
FIG. 1a is an anterior view of the femoral component of FIG. 1 showing the proximal tissue ingrowth area including a distal boundary thereof.

Referring to FIG. 1 there is shown a known femoral component for implantation into the proximal end of the femur (not shown) generally denoted as 10. Femoral component 10 includes a distal stem portion 12, a proximal portion 14, a neck portion 16 and a trunnion 18 for receiving a spherical head (also not shown). Proximal portion 14 includes a proximal shoulder 15 having a threaded bore 17. Bore 17 is usually used to couple to an inserter to locate the implant in the femoral canal upon initial implantation. Proximal portion 14 includes any known tissue ingrowth area which typically is a porous surface adapted to allow tissue from the canal of the femur to ingrow into the porous structure. FIG. 1a is an anterior view of femoral component 10 showing the anterior or posterior ingrowth area 19 (depending on whether the implant is a right or left hip) including a distal boundary 20.

Figure 2:
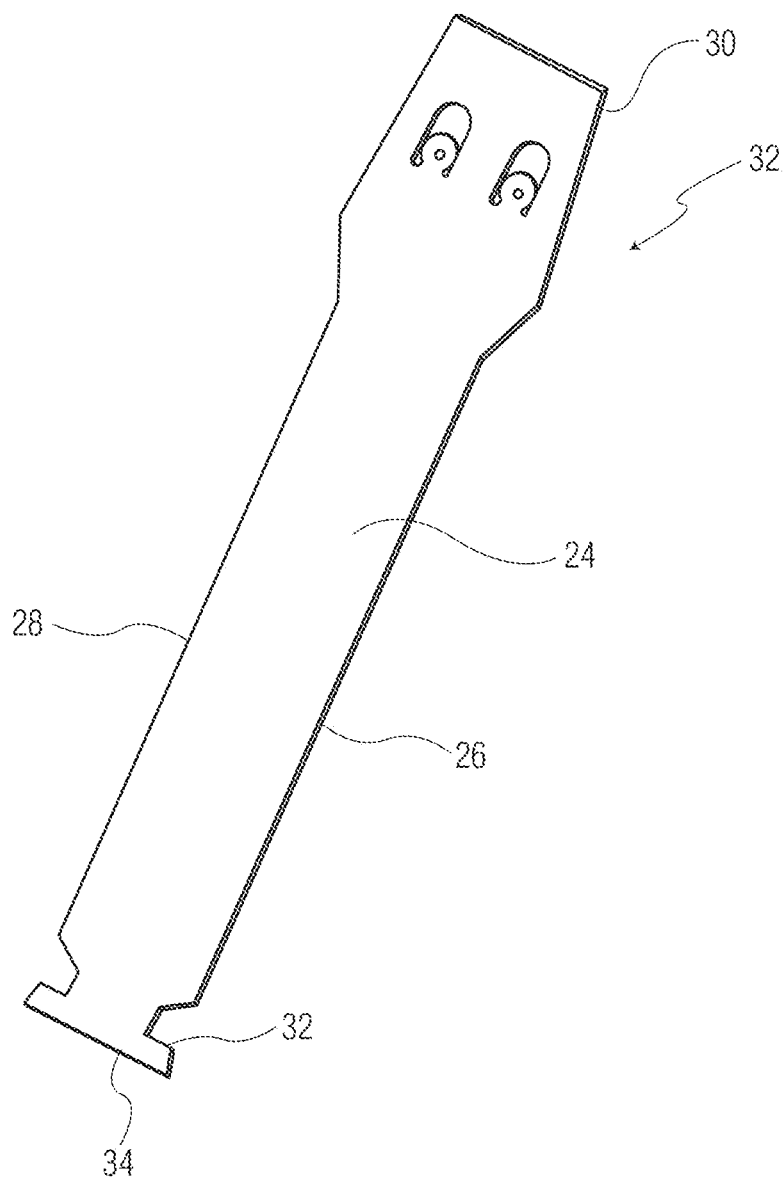
FIG. 2 is a prospective view of an oscillating saw blade utilized with the cutting block of the present invention.

Referring to FIG. 2, there is shown the oscillating sagittal saw utilized with the cutting guide of the present invention generally denoted as 22. Such a saw blade is disclosed in U.S. Patent Publication No. 2007/0119055, the disclosure of which is incorporated herein by reference. Oscillating saw blade 22 includes a guide housing 24 which includes side guide edges 26 and 28. Oscillating blade 22 includes a drive or proximal end 30 and an oscillating distal saw blade 32 having a series of teeth 34.

Figure 3:
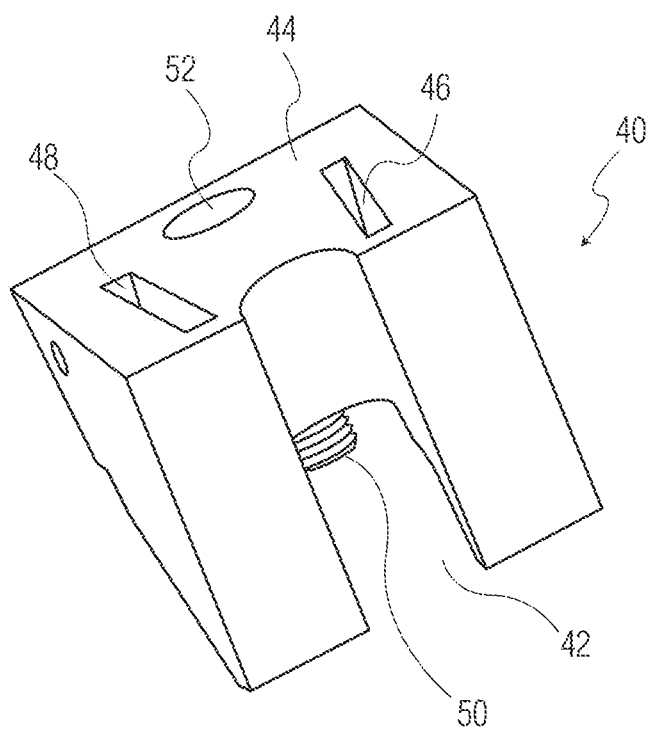
FIG. 3 is an isometric view of the cutting block of the present invention.

Referring to FIG. 3, there is shown a cutting block generally denoted as 40 having a cavity 42 for receiving the neck portion 16 of a femoral component 10 such as shown in FIG. 1. The proximal facing surface 44 of cutting block 40 includes a pair of saw blade guide slots 46 and 48. One slot 46, 48 is aligned with the anterior or posterior surface 19 of femoral component 10. A threaded attachment element 50 extends from upper surface 44 through a bore 52 therein and is designed to couple through threaded bore 17 in proximal shoulder 15 of implant 10 as shown in FIG. 1.

Figure 4:
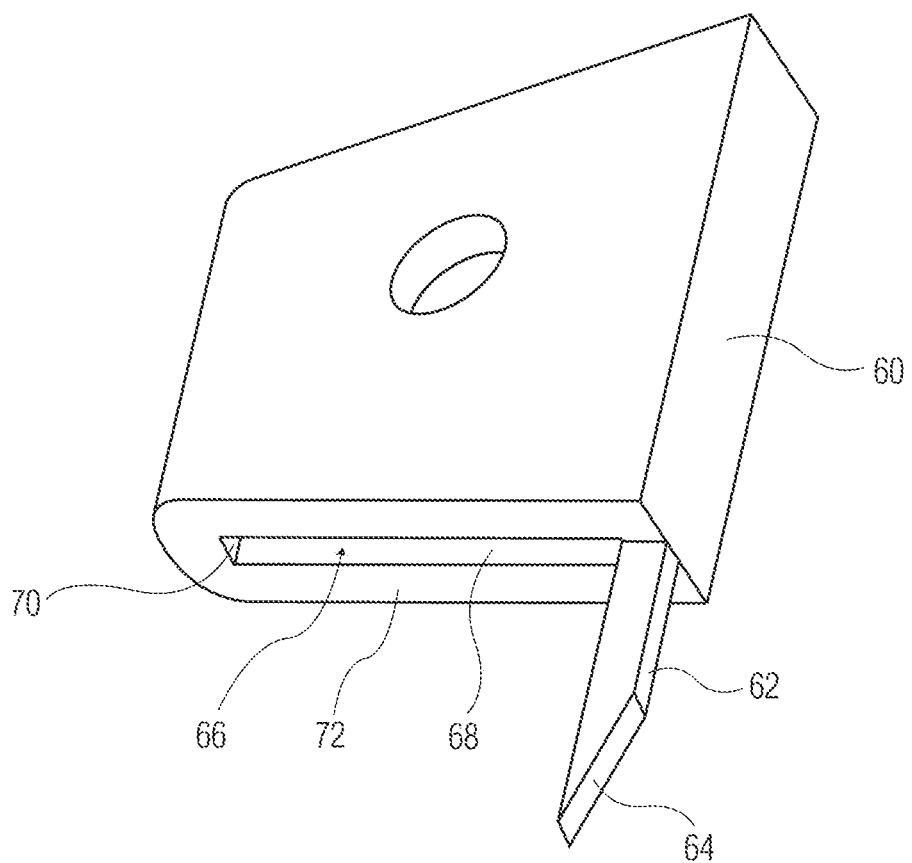
FIG. 4 is an isometric view of the cam element of the present invention mounted on the saw blade of FIG. 2.

Referring to FIG. 4, there is shown a cam element generally denoted as 60 having a guide arm 62 including a tapered leading tip 64. Cam element 60 includes a rectangular slot 66 for receiving the housing 24 of the oscillating saw blade 22 of FIG. 2. Rectangular opening 66 has parallel walls 68 extending along the width of housing 24 and end walls 70 extending parallel to the edges of housing 24. The rectangular area 72 which extends around opening 66 is designed to contact the top surface 44 of cutting block 40 to limit the movement of the saw blade within the femur.

Figure 4A:
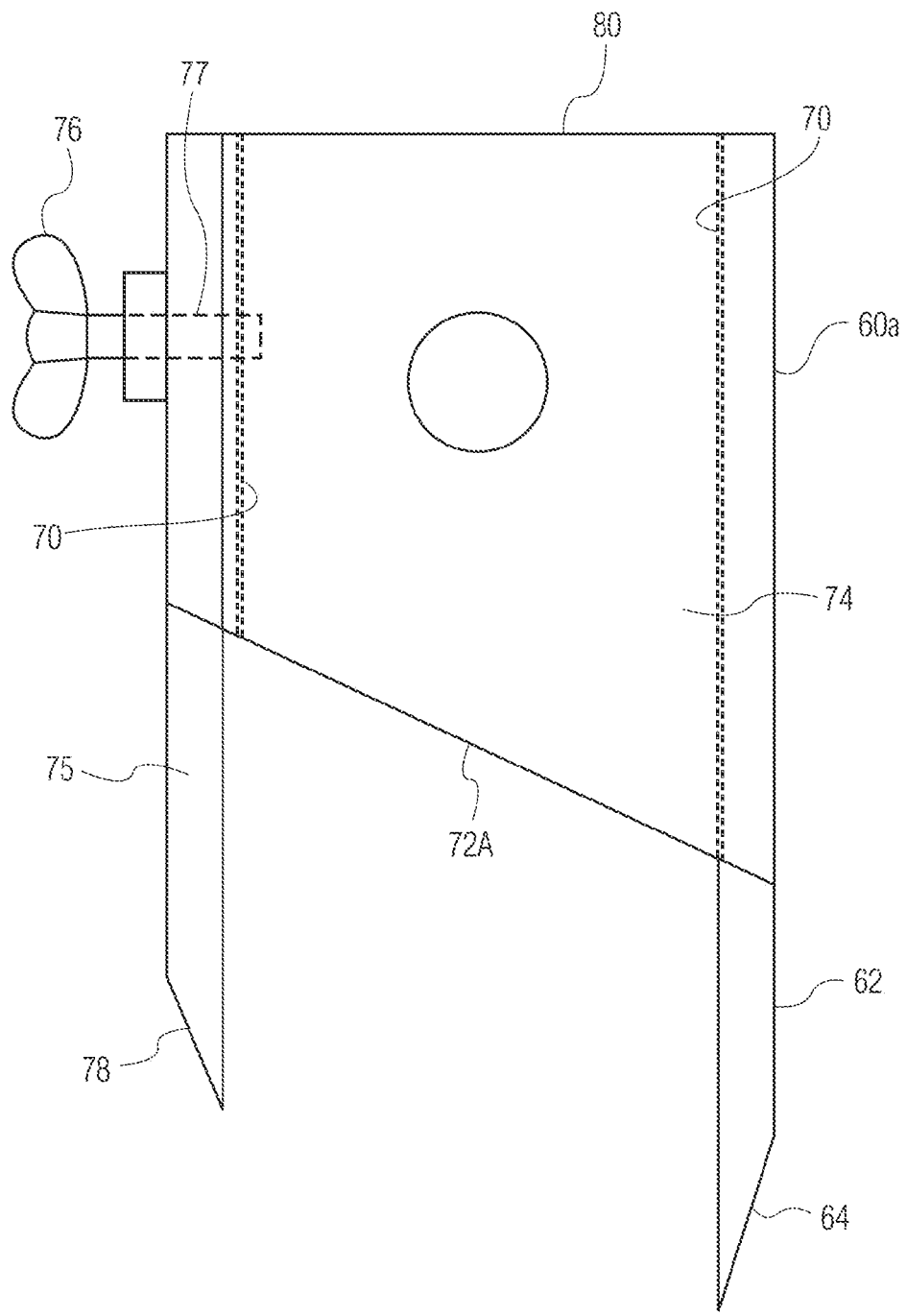
FIG. 4a is a front view of the cam element of FIG. 4.

Referring to FIG. 4A there is an elevation view of an alternate cam element 74 similar to that of FIG. 4 showing a second cam arm 75 and a thumb screw 76 in threaded through bore 77 adapted to contact housing 24 of saw 22 in order to hold cam element 74 thereon. Second cam arm 75 of cam element 74 includes a tip 78. Preferably only one guide arm 62 or 75 is utilized on cam element 60 or 74 but both can be used. As can be seen in FIG. 4A, the bottom surface 72A of cam element 74 extends at an angle to top surface 80 of cam element 74.

Figure 5:
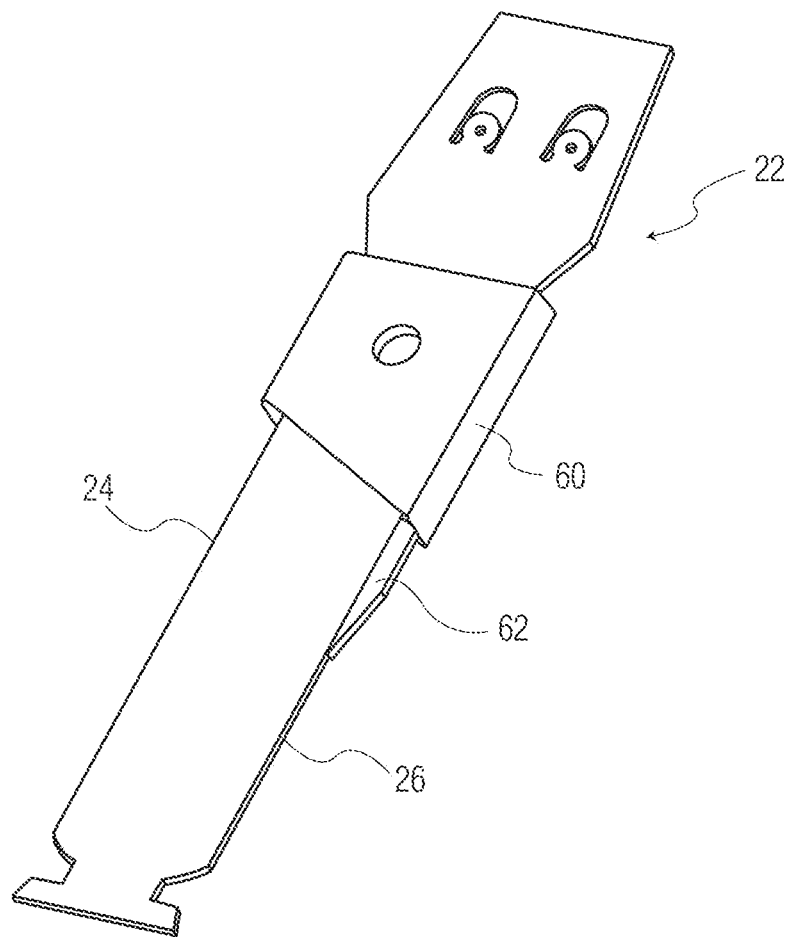
FIG. 5 is an isometric view of the cam element of FIGS. 4 and 4a mounted on the oscillating saw blade of FIG. 2.

Referring to FIG. 5, there is shown cam element 60 including guide arm 62 mounted on a housing 24 of saw 22. Saw 22 is in all respects the same as that shown in FIG. 2. The inner wall 70 as shown in FIG. 4A contacts the outer edges 26 of saw 22.

Figure 6:
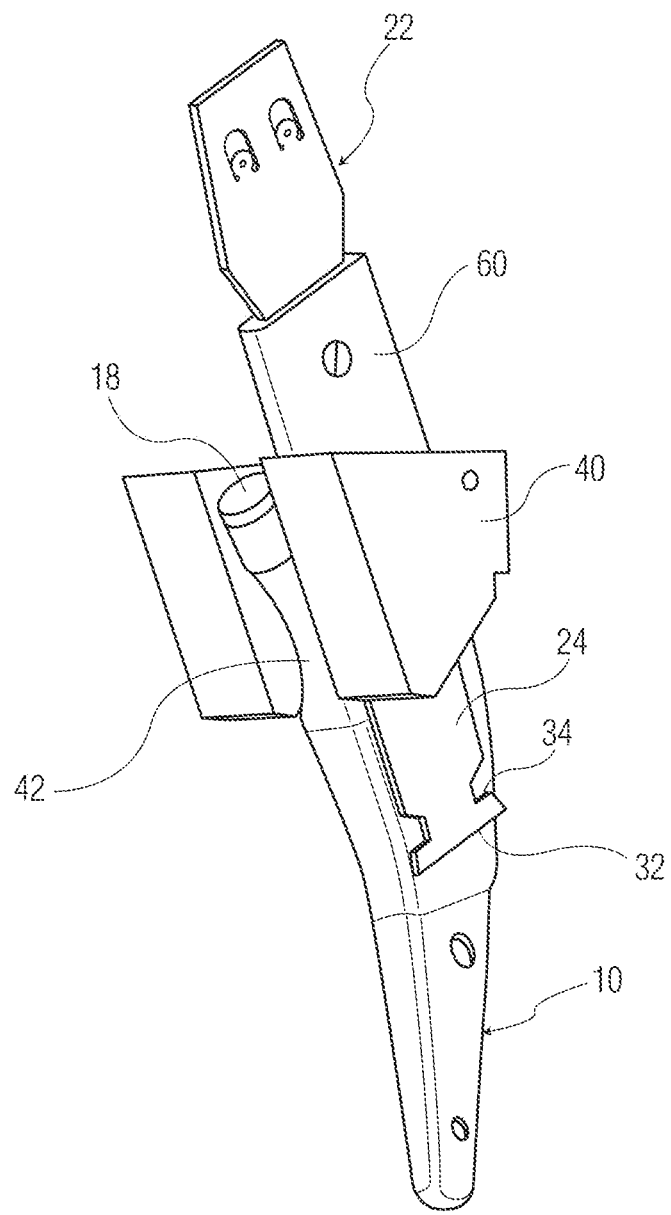
FIG. 6 is an isometric view of the oscillating saw blade, cam element and guide block of FIGS. 2, 3 and 4 mounted on the femoral component of FIG. 1.

Referring to FIG. 6 there is shown an assembly of cutting block 40 mounted on femoral component 10 of FIG. 1 or 1a with the assembly of FIG. 5 extending into slot 46 and adapted to cut the anterior surface or posterior (depending on whether the component is a right or left) of femoral component 10 from the femur (not shown).

Figure 7:
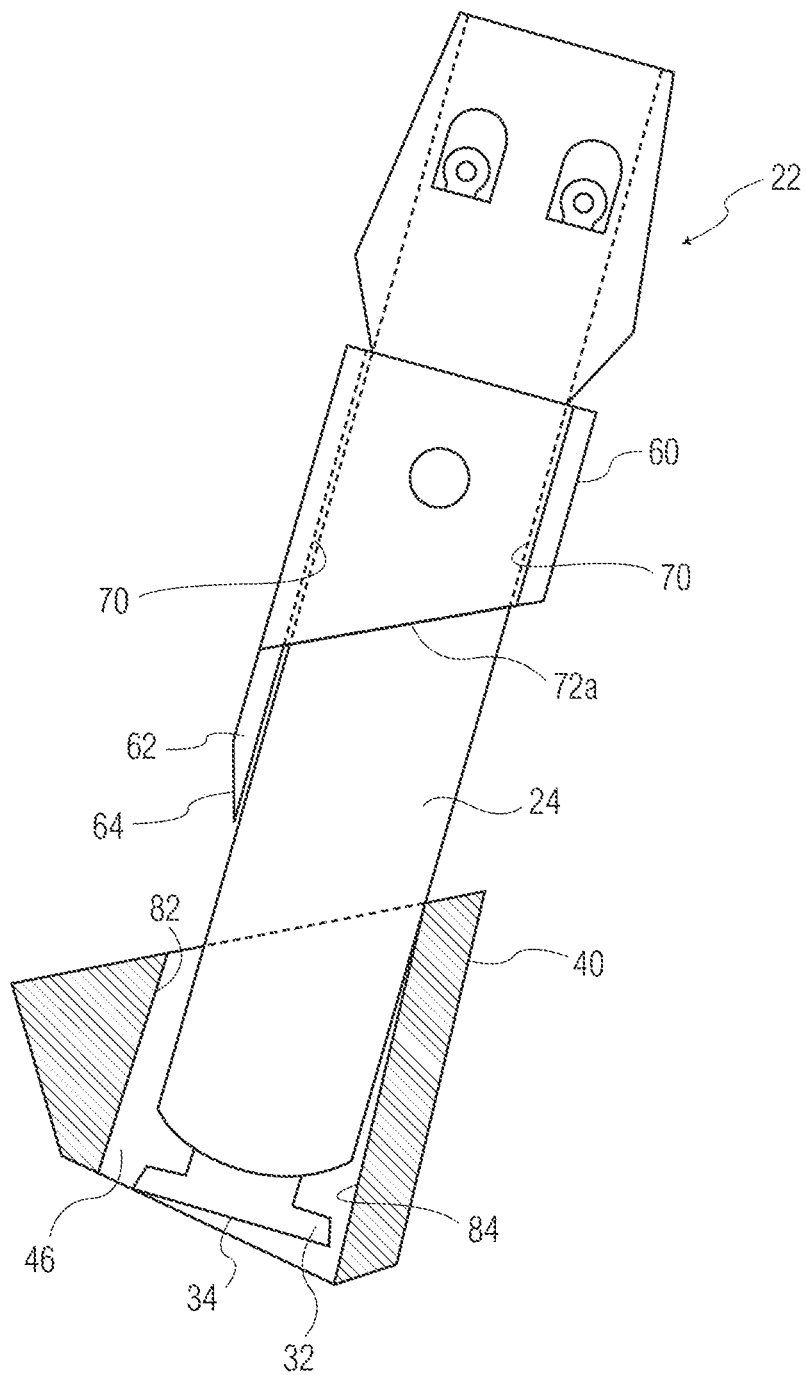
FIG. 7 is a cut away view of the guide block of FIGS. 3 and 3a with the cam element and oscillating saw extending through a slot in the cutting block.

FIGS. 7-10 show partial cross-sectional views of the assembly of FIG. 6 with saw 22 at various positions with respect to cutting block 40. In the view of FIG. 7 guide arm 62 and tip 64 of cam element 60 are shown prior to entering slots 46 or 48 of block 40. For purposes of explanation, the slot engaged will be considered as oriented to cut the anterior side of the component 10.

Figure 8:
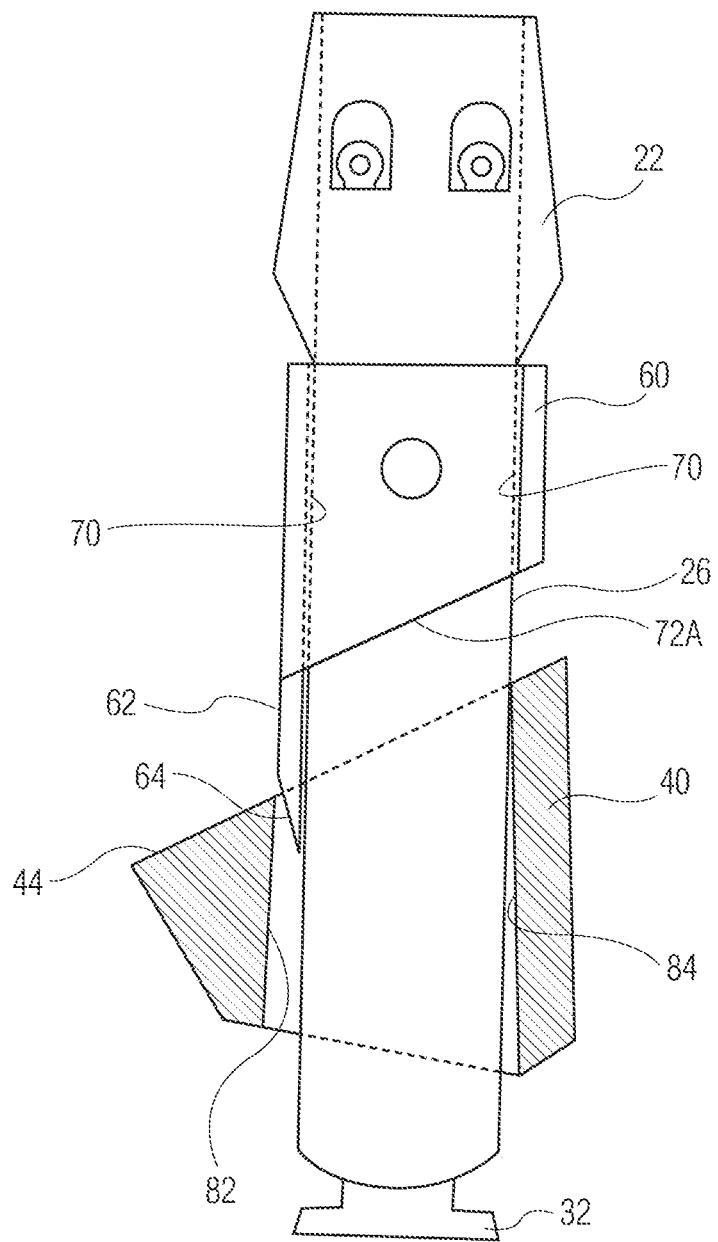
FIG. 8 is a view similar to FIG. 7 with the oscillating saw and cam element in a second position with the cutting guide.

FIG. 8 shows the assembly of FIGS. 6 and 7 with the guide arm 62 engaging the short end wall 83 on the lateral side of cutting block 40 as shown in FIG. 6. Tip 64 engages side wall 82 and as guide arm 62 is inserted deeper into slot 46, cutting end 32 of the oscillating saw 22 is rotated so as to maintain its alignment with the anterior tissue ingrowth surface of the femoral component 10. Sidewall 26 of blade housing 24 of sagittal saw 22 engages end 84 of slot 46, 48 as angle tip 64 engages wall 82. Obviously the distance between wall 82 and 84 of cutting guide 40 is wider than the width of housing 24 and walls 82, 84 may extend in a non-parallel relationship.

Figure 9:
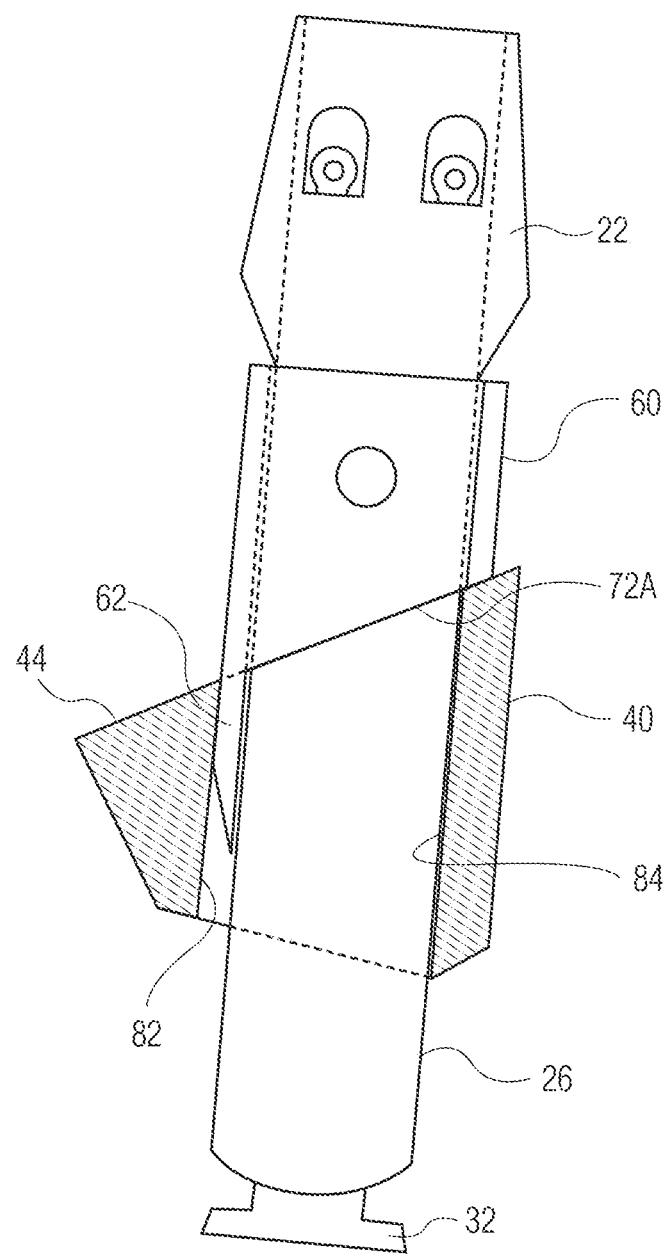
FIG. 9 is a cut away view of the guide of FIG. 3 with the cam element and oscillating saw in a third position with a stop surface on the cam element engaging a complimentary stop surface on the cutting guide.

Referring to FIG. 9 there is shown oscillating saw 22 inserted further into one of the slots 46 or 48 of cutting block 40 with guide arm 62 engaging wall 82 of slots 46, 48 and the edge 26 fully engaging wall 84 of the slots. Also shown is stop surface 72A of cam element 60 is now in contact with proximally facing surface 44 of the cutting block which limits further penetration of the sagittal saw 22 into the femur.

Figure 10:
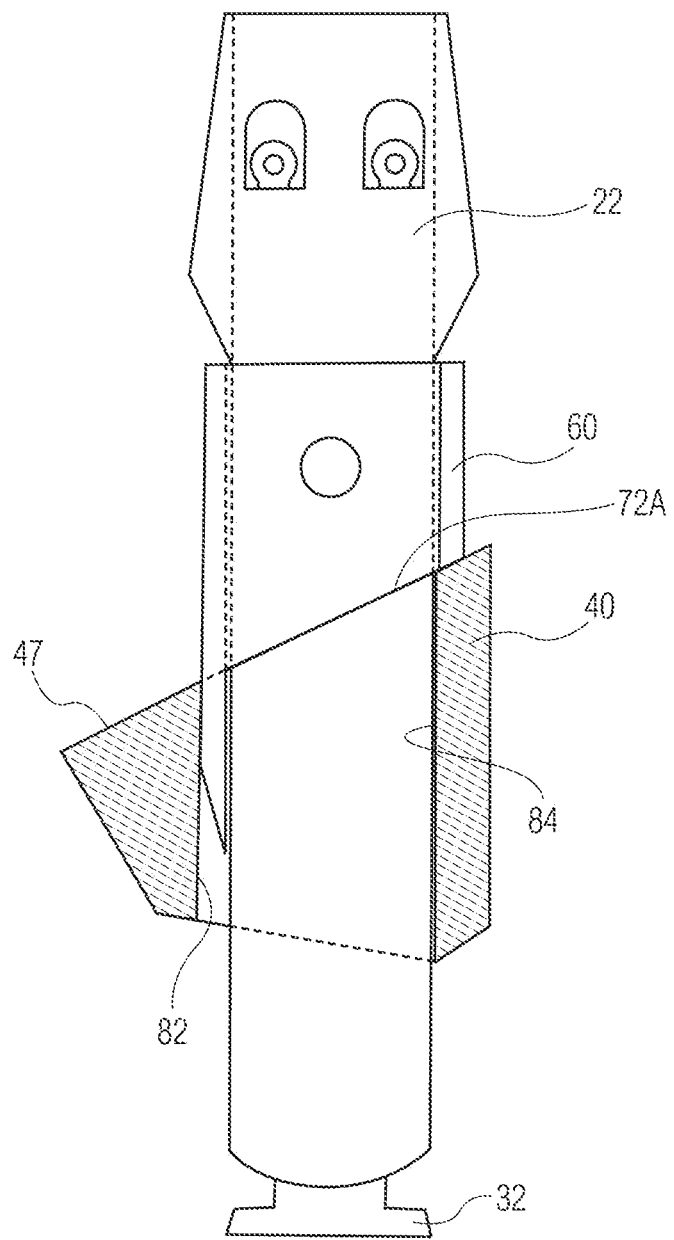
FIG. 10 is a view similar to FIG. 9 with the cutting blade guide housing in a second position.

Referring to FIG. 10 there is shown an alternate design for surfaces 82, 84 of a cutting block 40 in which wall is angled away from wall 84 on moving from a proximal to distal direction.

Figure 11:
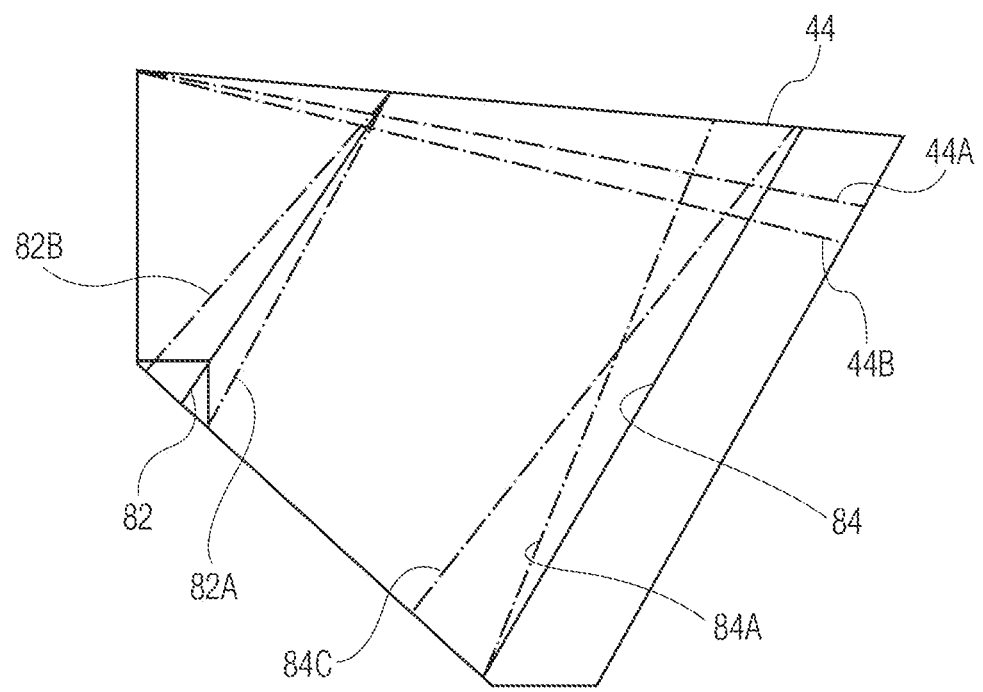
FIG. 11 is a cross-sectional view of the cutting guide of FIG. 3 showing various possible configurations of the stop and guide surfaces.

Referring to FIG. 11 there is shown a cutting block 40 with a series of possible slot configurations for end walls 82, 84 designed to guide saw 22 along the medial and lateral side tissue ingrowth junctions of the anterior and posterior surfaces of the femoral component and the femur. These walls are labeled 82, 82A, 82B and the opposite walls are labeled 84, 84A and 84B. The wall angles would be dictated by the shape of the proximal femoral component and located such that oscillating saw tip 34 is limited to resecting the bone until the medial-lateral edge margins of the femoral component are reached. As shown, the top surface of the block may be angled to vary the proximal distal depth of the saw cut by changing the point where the surface 72 of the cam element engages upper surface 44 of the cutting block. Such alternate surfaces are labeled 44A and 44B.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone resection system comprising:
a prosthetic implant having an anterior and posterior outer surface capable of attaching to bone;
a cutting guide having guide surfaces thereon mountable on the prosthetic implant, the guide surfaces are alignable with the implant anterior and posterior outer surfaces;
a saw comprising a housing having spaced apart first and second sides joined by first and second edge surfaces and having a proximal end and a distal end, a cutting head drive system on the housing, the cutting head drive system driving a cutting head having teeth extending outwardly of the distal end of the housing; and
a cam element mounted on the saw housing intermediate the proximal and the distal ends, the cam element having a distal end with a guide arm extending therefrom engagable with at least one of the guide surface on the cutting guide, the cam element having a stop surface for engaging a stop surface on the cutting guide.

2. The bone resection system as set forth in claim 1 wherein the guide surfaces have opposed first and second end surfaces extending generally perpendicular to the implant outer surface for engaging the first and second sides of the housing, the first and second end surfaces oriented at an angle to one another respectively.

3. The bone resection guide as set forth in claim 2 wherein the prosthetic implant is a prosthetic femoral component having a neck portion coupled to a distally extending stem portion and the cutting guide is mountable adjacent the neck portion.

4. The bone resection system as set forth in claim 3 wherein the guide surface of the cutting guide is aligned with anterior and posterior sides of the femoral component.

5. The bone resection system as set forth in claim 4 wherein the cutting guide includes a passageway for receiving the neck portion of the femoral component.

6. The bone resection system as set forth in claim 4 wherein the cutting guide has an anterior opening and a posterior opening respectively aligned with the anterior and posterior outer surfaces of the femoral component.

7. The bone resection system as set forth in claim 5 wherein the cam element medial and lateral opening is a rectangular opening for receiving an outer surface of the housing, the rectangular opening formed by two end walls and two longer sidewalls, the two end walls are connected medially and laterally with respect to the implant and contacting the first and second sides of the housing, the guide arm extending from one end wall.

8. The bone resection system as set forth in claim 6 wherein the guide arm has a leading surface with an outer surface tapered towards the housing and forming a tip adjacent the housing.

9. The bone resection system as set forth in claim 6 further comprising an attachment element extending between the cam element and the housing for locking the cam element on the housing.

10. The bone resection system as set forth in claim 7 wherein the two longer sidewalls of the rectangular opening slidable receive the housing first and second sides.

11. The bone resection system as set forth in claim 10 wherein a distance between the end walls of the rectangular opening is greater than a distance between the edges of the housing.

12. The bone resection system as set forth in claim 1 wherein the cutting guide includes a fastener for coupling the cutting guide to the prosthetic implant.

13. The bone resection system as set forth in claim 1 wherein the cam element includes means for fixing it to the housing.

14. The bone resection system as set forth in claim 1 wherein the cutting head teeth oscillate with respect to the saw housing.

* * * * *